United States Patent [19]

Schuster, Jr. et al.

[11] 4,071,684

[45] Jan. 31, 1978

[54] PROCESS FOR PRODUCING 3-SUBSTITUTED 1,2,4-TRIAZINES

[75] Inventors: Albert J. Schuster, Jr., Midland, Mich.; John Martin, Carmel, Ind.

[73] Assignee: The Dow Chemical Company, Midland, Mich.

[21] Appl. No.: 761,177

[22] Filed: Jan. 21, 1977

[51] Int. Cl.$^2$ .......................................... C07D 253/06
[52] U.S. Cl. .................................................... 544/182
[58] Field of Search ................................. 260/248 AS

[56] References Cited

U.S. PATENT DOCUMENTS 3,471,486   10/1969   Trepanier ............................. 260/248

Primary Examiner—John M. Ford
Attorney, Agent, or Firm—James W. Ambrosius

[57] ABSTRACT

A process for producing 3-substituted 1,2,4-triazines comprising reacting a nitrile with a 2-aminoethylhydrazine in the presence of a catalytic amount of a transition metal salt or elemental sulfur.

5 Claims, No Drawings

PROCESS FOR PRODUCING 3-SUBSTITUTED 1,2,4-TRIAZINES

BACKGROUND OF THE INVENTION

Various substituted 1,4,5,6-tetrahydro-1,2,4-triazines are described as having antidepressant properties in U.S. Pat. No. 3,471,486. In general the compounds are prepared by reacting an imino ester hydrohalide dissolved in glacial acetic acid, methanol or ethanol with a 2-aminoalkylhydrazine. This method of preparing the compounds is tedious and gives poor yields making the overall procedure uneconomical for commercial production. The present invention is directed to a new synthetic route which can be used to prepare triazines of the type described above.

In related art substituted 2-imidazolines have been synthesized by the cyclization of a diamine with a nitrile in the presence of elemental sulfur. *Nippon Kagaku Zasshi* 1968, 89 (8), 780 (Chem. Abs. 70:19983q.)

SUMMARY OF THE INVENTION

The present invention is directed to a process of preparing a 3-substituted 1,2,4-triazine which comprises reacting a nitrile with a 2-aminoethylhydrazine or substituted 2-aminoethylhydrazine in the presence of a catalytic amount of a transition metal salt or elemental sulfur. The process is particularly useful in preparing a triazine having the general formula

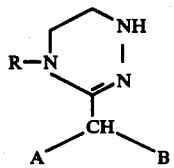

wherein R is hydrogen or methyl and A and B independently represent hydrogen, alkyl of from 1 to 5 carbon atoms, phenyl, substituted phenyl, benzyl, or substituted benzyl. Substitutions on the phenyl and benzyl rings described above may include almost any group which will not react with hydrazine under the conditions of the reaction process. Such substitutions include halo, lower alkyl, lower alkoxy, nitro, napthyl and pyridyl. As used herein lower alkyl and alkoxy refers to a group having from 1 to 3 carbon atoms.

The reaction of the nitrile with 2-aminoethylhydrazine can be carried out in a suitable solvent system, usually a high boiling alcohol, but the reaction can also be carried out in the absence of solvent by simply mixing the reactants together with a catalytic amount of a transition metal salt or elemental sulfur. The reaction usually proceeds more rapidly in the absence of solvent, but when the product is made in large batches, it is often desirable to use some solvent to lower the viscosity of the reactants to facilitate mixing. As used herein the term catalytic amount refers to the amount of transition metal salt or elemental sulfur required to convert equimolar amounts of the hydrazine and the nitrile to the 1,2,4-triazine product. The transition metal salts, ferric chloride and zinc acetate were found to give satisfactory results. Elemental sulfur is particularly preferred because of its ready availability, and it evolves out of the reaction mass leaving only trace amounts in the final product.

The general reaction described above may be represented as follows

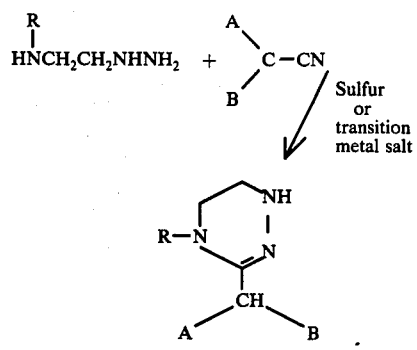

DETAILED DESCRIPTION OF THE INVENTION

As noted above sulfur was found to be the preferred catalyst in carrying out the process which is the subject of the present invention. The reaction is generally carried out at a temperature of from 70° to 100° C with from 85° to 95° C being preferred. Lower temperatures are operable but the rate of reaction is slowed down. Temperatures above about 120° C cause the hydrazine/sulfur complex to vaporize out of the reaction mixture and lead to decreased yields and the formation of impurities.

The compound 3-(1,2-diphenylethyl)-1,4,5,6-tetrahydro-1,2,4-triazine is an effective antidepressant drug. Production of this compound in experimental developmental studies in both small laboratory and large production size batches using the process of this invention has been carried out and are summarized below.

The compound 3-(1,2-diphenylethyl)-1,4,5,6-tetrahydro-1,2,4-triazine is most conveniently prepared by a two step synthesis, the second step being the novel process which is the subject of this invention. In the first step the intermediate 2,3-diphenylpropionitrile is produced by a phase transfer catalysis reaction involving benzyl cyanide and benzyl chloride in the presence of aqueous sodium hydroxide. Reactions of this general type are well documented in the literature. See *Synthesis*, 441–456, August 1973 and Polish Pat. No. 47,950 (CA61:14 593q). In the second step the 2,3-diphenylpropionitrile and 2-aminoethylhydrazine are cyclized in the presence of sulfur to yield the 3-(1,2-diphenylethyl)-1,4,5,6-tetrahydro-1,2,4-triazine. The triazine readily may be converted to the hydrohalide salt if desired by acidification with a pre-selected hydrohalide. The intermediate nitrile can be produced by other known methods (see, for example, Tetrahedron Letters No. 14, pp 1509–1511, 1966) and such intermediates are entirely satisfactory for use in the second step of the synthesis described above.

The following examples will serve to further clarify the present invention and will serve to illustrate certain preferred embodiments thereof; however, they are not to be construed as a limitation upon the scope of the invention.

EXAMPLE 1

Preparation of
3-(1,2-diphenylethyl)-1,4,5,6-tetrahydro-1,2,4-triazine
monohydrochloride Step one: A reaction vessel consisting of a 2 liter round bottom flask fitted with a mechanical stirrer, thermometer, nitrogen inlet and reflux condenser was charged with 585 g (574 ml; 5.0 moles) of benzyl cyanide, 250 ml of 50% sodium hydroxide and 12.5 g (0.055 mole; 4.4 mole %) of benzyltriethylammonium chloride. While maintaining the temperature at about 50° C in a cool water bath, 224.4 g (1.77 mole) of benzyl chloride was slowly added dropwise over a period of about 1 hour. The reaction mass was stirred for an additional 1 hour after which 400 ml of deionized water was added to dissolve the sodium chloride and caused a separation of the aqueous and organic layers. In this step if an emulsion formed, methylene chloride was added. The organic layer was distilled to separate the 2,3-diphenylpropionitrile from the other reactants and impurities. The identity of the compound was confirmed by elemental analysis, NMR, IR, and mass spectrophotometry data.

Step two: The nitrile intermediate prepared in step one (35.0 g, 0.169 mole) was heated under nitrogen with 0.379 gram (0.012 gram-atom, 7 mole %) of sulfur to about 70° C in a 100 ml round bottom flask until the sulfur dissolved (about 2 hours). The reaction vessel was charged with 25.4 grams (0.338 moles; 2 equiv.) of 2-aminoethylhydrazine. The temperature was increased to about 100° C and held for about 5 hours. The reaction mass was cooled to about 50° C after which 75 ml of toluene was added followed by extraction with 75 ml of water. Absolute alcohol (35 ml) was added and the mixture refluxed while hydrogen chloride was bubbled into the flask. The 3-(1,2-diphenylethyl)-1,4,5,6-tetrahydro-1,2,4-triazine monohydrochloride crystallized out and was filtered off then washed with a 90/10 toluene/ethanol mixture. The product was dried in vacuo. Elemental analysis, X-ray crystallography, NMR, and mass spectrophotometry were used to confirm the structure.

Using the general procedure outlined above, a number of related compounds were prepared having the general structure

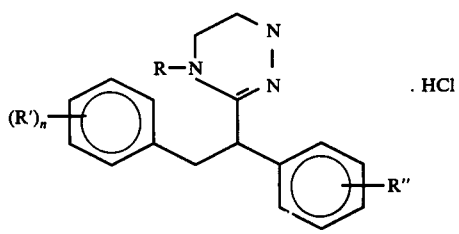

wherein n is the integer 1 or 2. These compounds are shown in Table 1 below.

TABLE 1

| Compound Example Number | R | R' | R" |
|---|---|---|---|
| 2 | CH₃ | H | H |
| 3 | H | 3-Cl | H |
| 4 | H | 4-Cl | H |
| 5 | H | 4-F | H |
| 6 | H | H | 2-napthyl |
| 7 | H | 3-F | H |

TABLE 1-continued

| Compound Example Number | R | R' | R" |
|---|---|---|---|
| 8 | H | 4-F | 4-OCH₃ |
| 9 | H | H | 4-CH₃ |
| 10 | H | 4-CH₃ | H |
| 11 | H | 3-CH₃ | H |
| 12 | H | H | 4-OCH₃ |
| 13 | H | H | 3-CH₃ |
| 14 | H | 4-NO₂ | H |
| 15 | H | H | 1-napthyl |
| 16 | H | 2,6-di Cl | H |
| 17 | H | 3,4-di Cl | H |
| 18 | H | 3,4-di OCH₃ | H |
| 19 | H | 1-napthyl | H |
| 20 | H | 3,4-di CH₃ | H |
| 21 | H | 2-pyridyl | H |
| 22 | H | 4-pyridyl | H |
| 23 | H | 2-napthyl | H |
| 24 | H | 2-napthyl | 2-napthyl |

In addition to the compounds listed above, compounds which do not fit the general formula of Table 1 were prepared using the process of the invention. The compounds include: 3-(1-(1,3-benzodioxol-5-yl)-2-phenylethyl)-1,4,5,6-tetrahydro-1,2,4-triazine monohydrochloride; 1,4,5,6-tetrahydro-3-(2-naphthalenylmethyl)-1,2,4-triazine monohydrochloride; and 3-(2-(4-chlorophenyl)-1-((4-methylphenyl)sulfonyl)ethyl)-1,4,5,6-tetrahydro-1,2,4-triazine.

EXAMPLE 25

Using essentially the same procedures outlined above, two batches containing 25.5 kg and 26.5 kg of 3-(1,2-diphenylethyl)-1,4,5,6-tetrahydro-1,2,4-triazine monohydrochloride were produced. The crude yield was found to be 65.1 and 70.0%, respectively. Following recrystallization from ethanol the yield of purified product was 42.5 and 53.1%, respectively.

It was found that the sulfur catalyst could be added directly to the melted nitrile without the lengthy heating needed to dissolve the sulfur in step two of the reaction. Thus overall batch time was significantly reduced from that of Example 1 above.

We claim:

1. A process for preparing a 3-substituted 1,2,4-triazine which comprises reacting a nitrile with 2-aminoethylhydrazine in the presence of a catalytic amount of a transition metal salt or elemental sulfur wherein the 2-amino-ethylhydrazine is represented by the formula

and the nitrile is represented by the formula

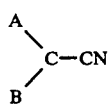

wherein R is hydrogen or methyl and A and B independently represent hydrogen, an alkyl of from 1 to 5 carbon atoms, phenyl, substituted phenyl, benzyl, or substituted benzyl; said substitutions on the phenyl and benzyl rings being selected from the group consisting of halo, lower alkyl, lower alkoxy, nitro, napthyl, and pyridyl thereby forming said triazine having the formula

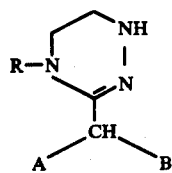

wherein A, B and R are as defined above.

2. The process of claim 1 wherein R is hydrogen, A is benzyl or substituted benzyl, and B is phenyl or substituted phenyl.

3. The process of claim 2 wherein the nitrile 2,3-diphenylpropionitrile is reacted with 2-aminoethylhydrazine.

4. A process for preparing 3-(1,2-diphenylethyl)-1,4,5,6-tetrahydro-1,2,4-triazine which comprises reacting benzyl cyanide with benzyl chloride to produce 2,3-diphenylpropionitrile and cyclizing the 2,3-diphenylpropionitrile with 2-aminoethylhydrazine in the presence of a catalytic amount of elemental sulfur to give 3-(1,2-diphenylethyl)-1,4,5,6-tetrahydro-1,2,4-triazine.

5. The process of claim 4 further comprising the step of acidifying the 3-(1,2-diphenylethyl)-1,4,5-tetrahydro-1,2,4-triazine with a hydrohalide to produce a hydrohalide salt thereof.

* * * * *